US005479797A

United States Patent [19]

Peterson

[11] Patent Number: 5,479,797

[45] Date of Patent: Jan. 2, 1996

[54] UNIDIRECTIONALLY SIZEABLE BRACELET ASSEMBLY AND CLOSURE MEANS THEREFOR

[75] Inventor: Dean D. Peterson, Canoga Park, Calif.

[73] Assignee: Precision Dynamics Corporation, San Fernando, Calif.

[21] Appl. No.: 91,260

[22] Filed: Jul. 15, 1993

[51] Int. Cl.$^{6}$ .............................. A61B 5/103; A44C 5/00

[52] U.S. Cl. .............................. 63/3; 63/1.1; 24/16 PB; 40/633

[58] Field of Search .................... 63/3, 2, 1.1; 24/16 PB, 24/30.5 P; 40/633, 665

[56] References Cited

U.S. PATENT DOCUMENTS

| | | | |
|---|---|---|---|
| 3,106,028 | 10/1963 | Baumgartner | 63/3 |
| 3,279,107 | 10/1966 | Baumgartner | 40/633 |
| 3,800,450 | 4/1974 | Laugherty | 63/3 |
| 4,272,900 | 6/1981 | MacLarty | 40/633 |
| 4,499,680 | 2/1985 | Coburn | 24/16 PB |
| 4,616,436 | 10/1986 | De Woskin | 24/16 PB |
| 5,031,943 | 7/1991 | Scott | 24/16 PB |
| 5,102,075 | 4/1992 | Dyer | 24/16 PB |
| 5,193,251 | 3/1993 | Fortsch | 24/30.5 P |

FOREIGN PATENT DOCUMENTS

| | | | |
|---|---|---|---|
| 1291172 | 10/1972 | United Kingdom | 24/16 PB |

OTHER PUBLICATIONS

A sample "Biologics" bracelet and literature.

*Primary Examiner*—Flemming Saether
*Attorney, Agent, or Firm*—J. Mark Holland; Thomas P. Mahoney

[57] ABSTRACT

A closure means for an identification band or bracelet includes integrally formed, unidirectionally engagement means to permit the bracelet to be further tightened, but not loosened, after assembly of the bracelet about a portion of a person or an object. In the preferred embodiment, the closure includes a body portion that is attached to a first end of the bracelet, and an opening to receive the second end of the bracelet after the bracelet has been placed in an encircling relationship about the person or object to be identified. The body portion is preferably configured as a sleeve having a rectangular cross-section, with one or more deformable mounting posts configured to be placed through a corresponding one or more mating openings in the first end of the bracelet and thereafter deformed to retain the first end of the bracelet on the body portion. Also in the preferred embodiment, the engagement means includes one or more protruding teeth having biting extremities adjacent the opening in the body portion. The teeth are oriented to permit the second end to slide past them as the end is inserted further through the opening, but to bite into the second end upon any attempt to withdraw it from the opening.

25 Claims, 2 Drawing Sheets

UNIDIRECTIONALLY SIZEABLE BRACELET ASSEMBLY AND CLOSURE MEANS THEREFOR

BACKGROUND OF THE INVENTION

This invention relates to closures for bracelets such as identification bands, and specifically to an improved closure which may be adjusted in one direction (such as for tightening the band) but not in an opposite direction (such as loosening the bracelet).

The use of identification bracelets is substantial, both in traditional areas such as hospital patient admissions and in relatively new applications such as crowd control and patron identification. Typically, such bracelets are assembled around a wearer's wrist and some attachment means affixes the ends of the band together in a fixed, non-changing circumference that is large enough to be comfortable for the wearer but small enough to prevent the band from being slipped over the wearer's hand. Identification bands can also be used to identify objects.

In certain applications, it is useful to provide a bracelet that can be affixed to a person or object and subsequently reduced in circumference, or "tightened". For example, newborn babies frequently lose weight and correspondingly lose "size" during the first few days after their births. Among other places, this "size" loss occurs in the wrists, hands, feet and ankles of the infant. As the infant's hands and feet "shrink" a fixed-circumference bracelet becomes looser and looser, eventually becoming so loose that it may be slipped over the infant's hand or foot. When this occurs, the bracelet ceases to function properly because it no longer identifies the infant with the intended degree of certainty, and may in fact completely cease to identify the infant (depending on whether the separated bracelet remains adjacent the infant or not). It therefore becomes desirable to reduce the likelihood that an identification bracelet assembly could be inadvertently slipped off of a newborn's wrist or ankle because of the reduced size of the infant's hand or foot.

One bracelet product that provides this "downsizability" is distributed by Bio-Logics Products, Inc. It incorporates a relatively complex, multi-part closure assembly including a roller, a ramped wedgelike insert, and a retaining sleeve having multiple openings therein. The roller and wedge insert are retained within the sleeve, and are intended to permit the bracelet to be tightened but not loosened.

In addition to the complex manufacture and assembly required for the Bio-Logics device, it can be manipulated rather easily after assembly so that it does not accomplish its intended purpose. Specifically, if the Bio-Logics device is oriented at the proper angle, gravity can pull the Bio-Logics roller element out of its "wedging" engagement, making it possible to loosen and even completely undo the Bio-Logics bracelet assembly (and thereby remove it from the person or object). Obviously, the Bio-Logics device (and all other bracelet devices of which the inventor is aware) leaves much to be desired in terms of addressing the needs for a reliable, adjustable bracelet of this type.

OBJECTS AND ADVANTAGES OF THE INVENTION

It is, therefore, an object of my invention to provide an improved, simpler and more reliable closure for identification bracelets, which permits the bracelet to be assembled about a wearer's wrist or other object to be identified, and subsequently to be tightened but not loosened. In its preferred embodiment, the closure includes a body portion, with attachment means on the body portion for attaching the first end of a band thereto. The closure further includes an opening in the body portion for receiving the second end of the band after the band encircles the person or object, and unidirectional gripping means such as engagement members formed integrally with the body portion for engaging the second end of the band after it has been inserted through the opening. The preferred engagement members are configured and oriented to permit further insertion of the second end of the band through the opening but to prevent detachment of the second end from the closure. In the preferred embodiment, this is accomplished by preventing retraction of the second end of the band from the opening.

An additional object of the invention is the provision of bracelet closure of the foregoing type, in which the unidirectional engagement means includes one or more protruding teeth that contact the second end of the band after the second end has been inserted a sufficient distance through the opening. The teeth are oriented to permit the second end of the band to slide past them as it is inserted further through the opening but to prevent retraction of the second end from the opening by "biting" into the second end when attempts are made to withdraw it from the opening.

Another object of my invention is the provision of a bracelet closure of the aforementioned character, which further includes an urging portion on the opposite side of the opening from the protruding unidirectional gripping engagement teeth. Among other things, the urging portion urges the second end of the band into operable abutting contact with the protruding teeth or other engagement means.

Yet another object of my invention is the provision of a bracelet closure of the aforementioned character in which the body portion of the closure constitutes a sleeve having an approximately rectangular cross-section, and having an upper wall, a lower wall, and two side walls connecting the upper wall and the lower wall to each other. In the preferred embodiment, the lower wall has one or more deformable mounting posts on a surface facing the upper wall, and the first end of the band means has one or more openings therein to matingly engage the mounting post or posts. After the first end has been mounted on the mounting post, the post is deformed to retain the first end thereon. The upper wall of the sleeve has an opening therein to facilitate the necessary deformation of the mounting post.

Still another object of my invention is the provision of a an identification bracelet assembly having a closure of the aforementioned character, in which the bracelet has a first end and a second end adapted to lie adjacent each other after the bracelet has been assembled in an encircling relationship about the object to be identified.

Other objects and advantages of the invention will be apparent from the following specification and the accompanying drawings, which are for the purpose of illustration only.

DESCRIPTION OF PREFERRED EMBODIMENT

Figure 1:
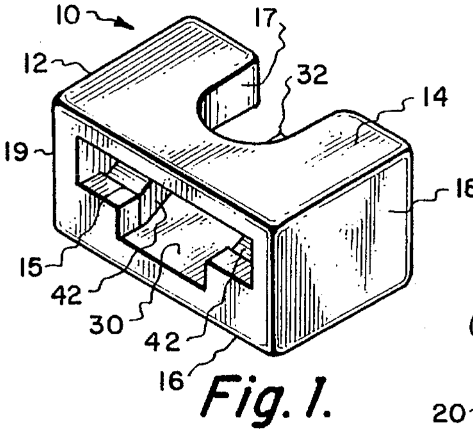
FIG. 1 is an isometric view of a preferred embodiment of a closure means constructed in accordance with the teachings of the invention.
Figure 2:
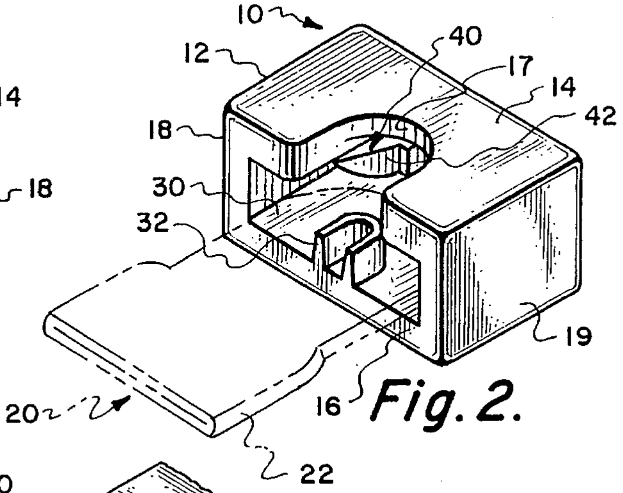
FIG. 2 is an isometric view of the other side of the embodiment of FIG. 1, also showing in phantom the preferred placement of a first end of a band means on a mounting post portion of the closure.

Referring to the drawings, and particularly to FIGS. 1 and 2 thereof, I show a preferred embodiment of a unidirectional closure means 10 for use with an identification bracelet or band 20 and constructed in accordance with the teachings of the invention. The closure means 10 is preferably manufactured as an integral piece of plastic or other suitably strong, lightweight material, by injection molding or other suitable process.

The band 20 is preferably fabricated from plastic or vinyl or other suitably flexible, lightweight material, and may be adapted to include identifying information thereon or to otherwise serve an identifying function relating to an object or person. The manufacture, design and identification features of bands such as band 20 are known and understood by those of ordinary skill in the art, and may include multi-layer laminates (see FIGS. 3–5, for example) or other constructions.

Those of ordinary skill in the art will also understand that the aforementioned identifying function can be accomplished in a wide variety of ways, including, by way of further example, placing identifying indicia on the closure means itself, color coding the band 20 and/or the closure means 10, etc.

The band 20 includes a first end 22 and a second end 24, FIGS. 3–6, remote from the first end 22. The band, as well as its first and second ends, is sized and shaped so that it can encircle the object or person to be identified (such as, for example, by encircling a person's wrist) and be usefully retained thereon. In the preferred embodiment, this retention is accomplished by unidirectionally adjustable closure means 10 which retains the first and second ends adjacent each other about the object, as will now be described in further detail.

The closure means 10 is preferably configured as a sleeve or body portion 12 having a generally rectangular cross-section. This cross-section is formed by an upper wall 14, a lower wall 16, and sidewalls 18 and 19 connecting the upper and lower walls 14 and 16.

Figure 3:
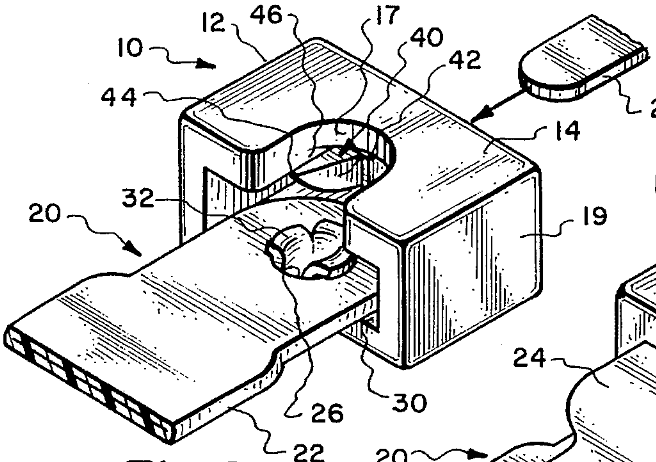
FIGS. 3 and 4 are isometric views, illustrating the preferred attachment of a first end of a band means on a mounting post portion of the closure and the insertion of a second end of the band means through an opening in the closure means.

The lower wall 16 has an upper surface 30 on which a mounting post 32 is disposed, preferably by integrally molding the mounting post 32 with the body portion 12. The band means 20 includes an opening 26 near the first end 22 of the band, which opening is configured to matingly engage the mounting post 32. After the end 22 has been mounted on the mounting post 32, FIG. 3, the mounting post 32 is preferably deformed such as by bending (as illustrated in FIG. 3) or otherwise, so that the first end 22 cannot be easily removed or detached from the body portion 12. To facilitate the deformation of the mounting post, the upper wall 14 preferably includes an opening 17 therein. The opening 17 facilitates automated or manual access to the mounting post with an appropriate tool to accomplish the deformation.

Those skilled in the art will understand that many varied methods of attachment could be effectively utilized to attach the first end 22 to the body portion 12, such as gluing, sonic welding or the like, and still be within the scope of my invention.

As a further example of alternative embodiments, a plurality of mounting posts (such as, for example, mounting post 32; a plurality is not shown in the drawings) could be provided integrally molded with the body portion 12. In such alternative embodiments, of course, band means 20 would include a correspondingly configured multiplicity of openings 26 to matingly engage the plurality of mounting posts. To facilitate the deformation of the plurality of mounting posts, the upper wall 14 would preferably include a corresponding plurality of openings 17 therein.

After the first end 22 has been attached to the body portion 12 of the closure means 10, the bracelet means 20 is assembled about the object or person to be identified. For applications such as those described above for newborn babies, the bracelet 20 is assembled about the newborn's wrist or ankle in an encircling relationship.

Figure 4:
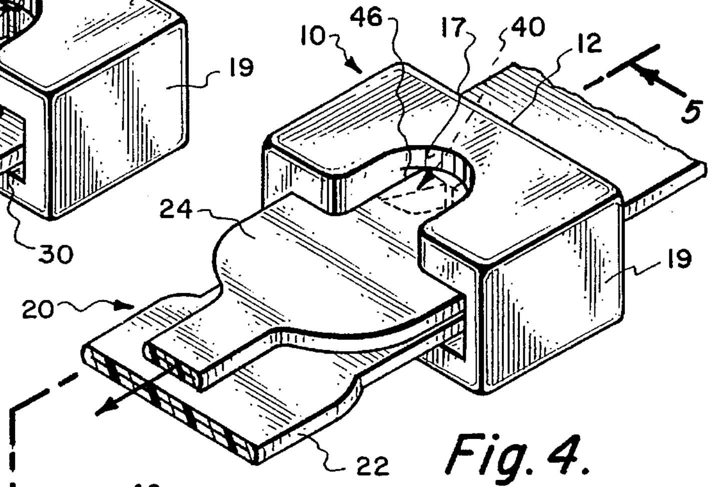
Figure 5:
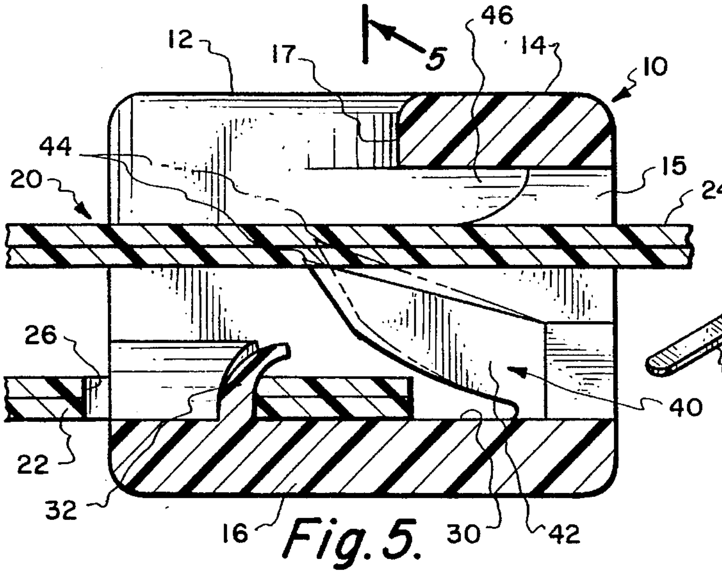
FIG. 5 is a sectional view of the bracelet and closure assembly, taken along line 5—5 of FIG. 4, and illustrating in phantom the "biting" action of the protruding teeth of the unidirectional engagement means.
Figure 6:
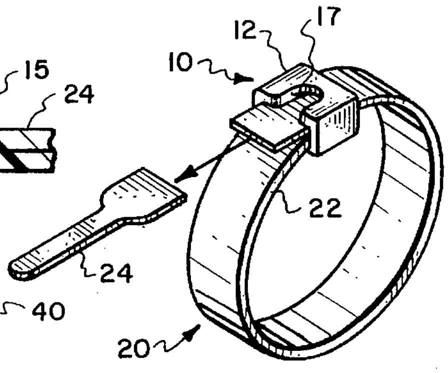
FIG. 6 is an isometric view of a preferred assembled bracelet and closure as it might appear after assembly about an object or a person's wrist, which also illustrates the severing of the excess length of the bracelet material after assembly.
Figure 7:
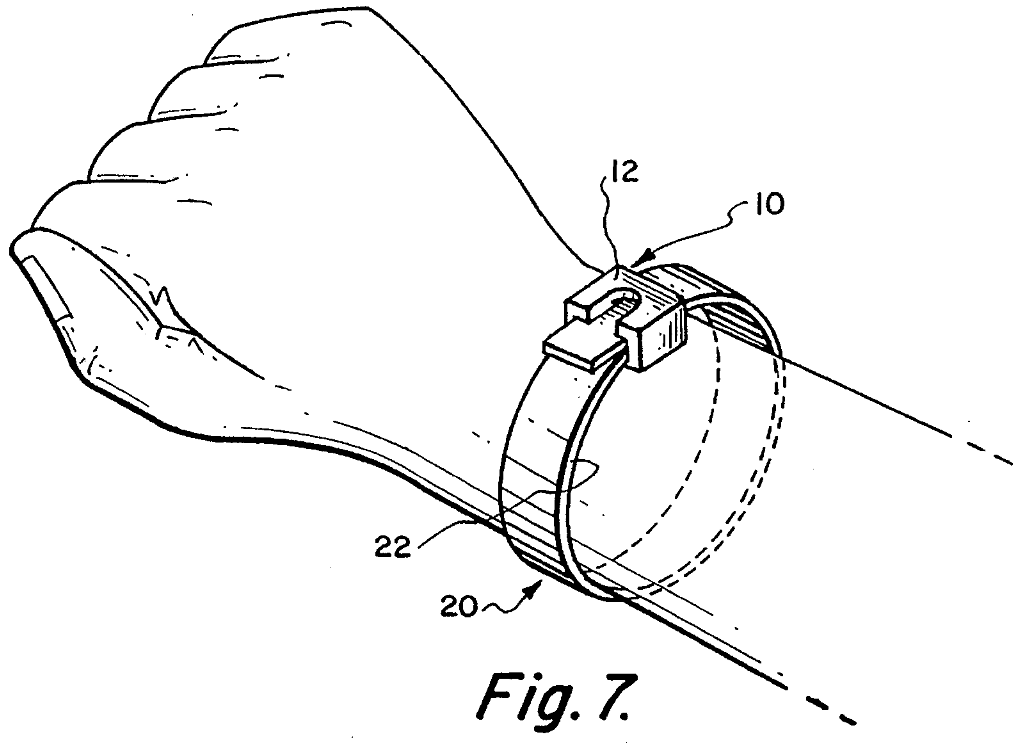
FIGS. 7 and 8 are isometric views similar to FIG. 6, but illustrate (respectively) a preferred bracelet assembly on a human wrist and the tightening of that bracelet assembly on that wrist.

After encircling the object to be identified, the second end 24, FIGS. 3 and 4, is inserted through an opening 15 (FIGS. 1 and 5) in the body portion or sleeve 12. The second end 24 can be inserted and pulled through the opening 15 in a first direction (as indicated by the arrows in FIGS. 3 and 4) until the bracelet forms a ring (see FIG. 6) of a desirable size. In the example of a newborn infant, the circumference of the ring is preferably large enough to permit the child to be comfortable but small enough so that the bracelet cannot easily be slipped over the infant's hand or foot. After the bracelet has been "sized" appropriately in this manner, excess length of the second end 24 can be severed from the rest of the bracelet by cutting or the like, FIG. 6. An example of such a bracelet on a human wrist is illustrated in FIG. 7.

Those skilled in the art will understand that the bracelet assembly can be removed from the object or person by, for example, cutting the band means 20 or by otherwise destroying or damaging the bracelet.

The second end 24 is retained by the closure means 10 by unidirectional gripping or engagement means 40 such as one or more engagement members or protruding teeth 42. The teeth 42 include biting extremities 44 and preferably are configured and oriented to protrude into the center of the sleeve 12 so that the extremities 44 contact the second end 24 of the band means 20. To facilitate and encourage this desired contact, the sleeve 12 preferably includes an urging portion 46 such as one or more curved shoulders, FIGS. 2–5. The urging portion 46 is configured and dimensioned to help urge the second end 24 against the biting extremities 44.

Those skilled in the art will understand that this desired contact between the second end 24 against the biting extremities 44 is necessary for the proper functioning of the invention. Where such contact occurs, attempts to move the second end 24 in a second and opposite direction (opposite the arrows shown in FIGS. 3 and 4) will cause the biting extremities 44 to "bite" into the second end 24. This prevents the disengagement of the second end 24 from the closure means 10, and thereby ensures the continued desired retention of the bracelet assembly on the wearer's wrist or about the object to be identified.

As indicated elsewhere herein, those skilled in the art will further understand that a wide variety of configurations can be effectively utilized in the closure 10 of my invention. By way of example and not by way of limitation, with respect to the mounting post or posts 32 and engagement members or protruding teeth 42, the precise number and combination of post or posts and a tooth or teeth may be any of a broad spectrum, and still permit the closure to be utilized with efficacy.

Figure 8:
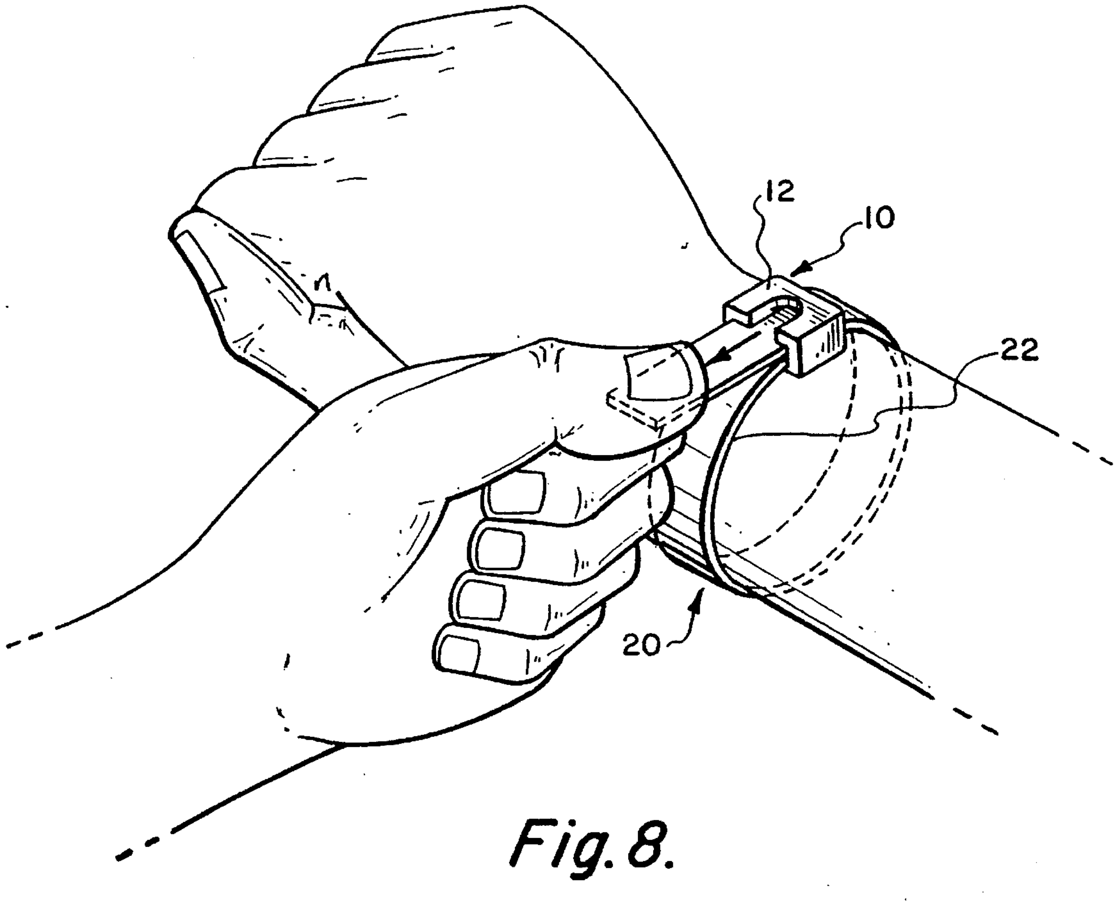

As described above, one important benefit of my invention is that it permits the second end 24 to slide further in the first direction relative to the closure means 10, but prevents any such relative motion in the second and opposite direction. As indicated above, this is of substantial benefit, for example, when a newborn child loses weight and its wrists, hands, feet and ankles "shrink". In such circumstances, the bracelet can simply be "tightened" an appropriate amount to ensure the desired retention of the bracelet on the infant. An example of such tightening is illustrated in FIGS. 7 and 8, with the tightening occurring in the direction indicated by the arrow touching the left thumb in FIG. 8.

This reduces the time, effort and expense that might otherwise be required to ensure the ongoing desired certainty of identification. Absent the use of such an adjustable bracelet, for example, it might be necessary to remove a first non-sizeable bracelet (for example, by cutting the band 20) and prepare and attach a second and smaller non-sizeable bracelet on the infant's wrist or ankle.

As indicated above, the teeth 42 are preferably fabricated integrally with the rest of the closure means 10. Because of this unitary fabrication, the unit cost for materials and assembly of the closure 10 and the complete bracelet assembly is reduced, and the overall manufacture and assembly process is simplified. Those skilled in the art will understand that the particular material from which the closure 10 is fabricated, and the specific dimensions of the teeth 42, the urging portion 46 and the opening 15 are selected to ensure the ready insertion of the second end 24 through the sleeve 12 as well as the desired engagement of the teeth 42 with the second end 24.

Among other things, the materials and dimensions of the teeth 42 and their biting extremities 44 must be such as to achieve the necessary contact between the teeth and the second end 24, even when no movement of the second end 24 relative to the closure means 10 occurs. In other words, to function properly, the teeth must be properly engaged with the second end 24 at all relevant times. Absent such proper engagement, the second end 24 could be withdrawn from the closure and the bracelet removed from the desired encircling relationship about the object or the wearer's wrist or ankle. Those skilled in the art will further understand that the thickness of the band or bracelet 20 is a factor in determining the specific dimensions of the teeth, etc.

Thus, by my invention, I provide a simple and inexpensive construction of an improved unidirectionally adjustable closure for bands such as identification bracelets.

The identification bracelet closure and assembly of my invention has been described with some particularity but the specific designs and constructions disclosed are not to be taken as delimiting of the invention in that various modifications will at once make themselves apparent to those of ordinary skill in the art, all of which will not depart from the essence of the invention and all such changes and modifications are intended to be encompassed within the appended claims.

I claim:

1. In an identification bracelet, the combination of: band means for encircling a portion of a person or an object to be identified, said band means having a first end and a second end adapted to lie adjacent each other in said encircling relationship; said second end having at least a portion thereof being a smooth surface; closure means having a body portion operably attached to said first end of said band means and adapted to receive and maintain said second end of said band means in said adjacent relationship; said closure means including unidirectional gripping means for gripping said second end of said band means to permit the movement of said second end in a first direction while preventing the movement of said second end in a second and opposite direction; in which said gripping means is formed integrally as a unitary structure with said body portion, said gripping means constituting infinitely adjustable gripping means capable of gripping said second end at any position along its length within a given range by biting into said smooth surface.

2. The identification bracelet of claim 1, in which said body portion includes an opening for receiving said second end of said band means, and said gripping means includes one or more unidirectional engagement members configured and oriented so that, after said second end of said band means has been inserted in said first direction through said opening and past said engagement members, retraction of said second end of said band means in said opposite direction is prevented by engagement between said engagement member or members and said second end.

3. The identification bracelet of claim 2 in which said closure means further includes an urging portion on the opposite side of said opening from said unidirectional engagement member or members, to urge said second end of said band means into operably abutting contact with said engagement members.

4. The identification bracelet of claim 2, in which said one or more unidirectional engagement members include a protruding tooth structure having a biting extremity in abutting contact with said second end of said band means after said second end of said band means has been inserted a sufficient distance through said opening, said biting extremity being oriented to permit said second end of said band means to slide past said biting extremity in said first direction but to prevent movement of said second end in said opposite direction by biting into said second end upon attempted movement of said second end in said opposite direction.

5. The identification bracelet of claim 4, in which said closure means further includes an urging portion on the opposite side of said opening from said unidirectional engagement member or members, to urge said second end of said band means into operably abutting contact with said engagement members.

6. The identification bracelet of claim 1 or claim 2 or claim 4 or claim 3 or claim 5, in which said closure means constitutes means for permitting the tightening of said band means about the person or object after the initial assembly of said band means about the person or object, in which said subsequent tightening can be to any size within said same or a similar given range.

7. The identification bracelet of claim 1 or claim 2 or claim 4 or claim 3 or claim 5, in which said body portion constitutes a sleeve having an approximately rectangular cross-section, said sleeve having an upper wall, a lower wall, and two side walls connecting said upper wall and said lower wall to each other; said lower wall having one or more deformable mounting posts on a surface facing said upper wall; and said first end of said band means having one or more corresponding openings therein to matingly engage said mounting post or posts, after which said mounting post or posts are deformed to maintain said operable attachment of said body portion to said first end of said band means.

8. The identification bracelet of claim 7, in which said upper wall includes one or more openings therein to facilitate said deformation of said mounting post or posts.

9. The identification bracelet of claim 7, in which said closure means constitutes means for permitting the tightening of said band means about the person or object after the initial assembly of said band means about the person or object, in which said subsequent tightening can be to any size within said same or a similar given range.

10. In a closure means for an identification band which band has first and second ends, the second end having at least a portion thereof being a smooth surface, and in which the band is adapted to encircle a portion of a person or an object to be identified, the combination of: a body portion; attachment means on said body portion for attaching the first end of the band to said body portion; an opening in said body portion for receiving the second end of the band after the band encircles the portion of the person or object; unidirectional engagement means formed integrally as a unitary structure with said body portion for engaging the second end of the band after it has been inserted through said opening, said engagement means being configured and oriented to permit further insertion of the second end of the band through said opening but to prevent retraction of the second end of the band from said opening, said engagement means constituting infinitely adjustable engagement means capable of engaging the second end at any position along its length within a given range by biting into the smooth surface.

11. The closure means of claim 10, in which said closure means further includes an urging portion on an opposite side of said opening from said unidirectional engagement means, to urge the second end of the band into operably abutting contact with said engagement means.

12. The closure means of claim 10, in which said unidirectional engagement means includes one or more protruding teeth having a biting extremity in abutting contact with the second end of the band after the second end has been inserted a sufficient distance through said opening, said biting extremity being oriented to permit the second end of the band to slide past said biting extremity as the second end is inserted further through said opening but to prevent retraction of the second end from said opening.

13. The closure means of claim 12, in which said closure means further includes an urging portion on an opposite side of said opening from said unidirectional engagement means, to urge the second end of the band into operably abutting contact with said engagement means.

14. The closure means of claim 10 or claim 12 or claim 11 or claim 13, in which said closure means constitutes means for permitting the tightening of said band means about the person or object after the initial assembly of said band means about the person or object, in which said subsequent tightening can be to any size within said same or a similar given range.

15. The closure means of claim 10 or claim 12 or claim 11 or claim 13, in which said body portion constitutes a sleeve having an approximately rectangular cross-section, said sleeve having an upper wall, a lower wall, and two side walls connecting said upper wall and said lower wall to each other; said lower wall having one or more deformable mounting posts on a surface facing said upper wall; and said first end of said band means having one or more corresponding openings therein to matingly engage said mounting post or posts, after which said mounting post or posts are deformed to maintain said operable attachment of said body portion to said first end of said band means.

16. The closure means of claim 15 in which said upper wall includes one or more openings therein to facilitate said deformation of said mounting post or posts.

17. The closure means of claim 15, in which said closure means constitutes means for permitting the tightening of said band means about the person or object after the initial assembly of said band means about the person or object, in which said subsequent tightening can be to any size within said same or a similar given range.

18. In a closure means for an identification band which band has first and second ends and has a portion associated with the second end which includes at least one smooth, non-serrated surface, in which the band is adapted to encircle a portion of a person or an object to be identified, the combination of: a body portion; attachment means to operatively attach the first end of the band to said body portion; an opening in said body portion tier receiving the second end of the band after the band encircles the portion of the person or object; and unidirectional engagement means formed integrally as a unitary structure with said body portion for biting into said at least one smooth, non-serrated surface of tile second end of tile band after tile end has been inserted through said opening.

19. The closure means of claim 18, in which said closure means further includes an urging portion on an opposite side of said opening from said unidirectional engagement means, to urge the second end of the band into operably abutting contact with said engagement means.

20. The closure means of claim 18, in which said unidirectional engagement means includes one or more protruding teeth having a biting extremity in abutting contact with the second end of the band after the second end has been inserted a sufficient distance through said opening, said biting extremity being oriented to permit the second end of the band to slide past said biting extremity as the second end is inserted further through said opening but to prevent retraction of the second end from said opening.

21. The closure means of claim 20, in which said closure means further includes an urging portion on an opposite side of said opening from said unidirectional engagement means, to urge the second end of the band into operably abutting contact with said engagement means.

22. The closure means of claim 18 or claim 20 or claim 19 or claim 21, in which said closure means constitutes means for permitting the tightening of said band means about the person or object after the initial assembly of said band means about the person or object, in which said subsequent tightening can be to any size within said same or a similar given range.

23. The closure means of claim 18 or claim 20 or claim 19 or claim 21, in which said body portion constitutes a sleeve having an approximately rectangular cross-section, said sleeve having an upper wall, a lower wall, and two side walls connecting said upper wall and said lower wall to each other; said lower wall having one or more deformable mounting posts on a surface facing said upper wall; and said first end of said band means having one or more corresponding openings therein to matingly engage said mounting post or posts, after which said mounting post or posts are deformed to maintain said operable attachment of said body portion to said first end of said band means.

24. The closure means of claim 23, in which said upper wall includes one or more openings therein to facilitate said deformation of said mounting post or posts.

25. The closure means of claim 23, in which said closure means constitutes means for permitting the tightening of said band means about the person or object after the initial assembly of said band means about the person or object, in which said subsequent tightening can be to any size within said same or a similar given range.

* * * * *

UNITED STATES PATENT AND TRADEMARK OFFICE

CERTIFICATE OF CORRECTION

PATENT NO. : 5,479,797

DATED : January 2, 1996

INVENTOR(S) : Dean D. Peterson

It is certified that error appears in the above-indentified patent and that said Letters Patent is hereby corrected as shown below:

In claim 18, column 8, line 14, replace "tier" with--for--; and line 19, replace "tile" in all three places with--the--.

Signed and Sealed this

Second Day of April, 1996

Attest:

Bruce Lehman

BRUCE LEHMAN

*Attesting Officer* *Commissioner of Patents and Trademarks*